United States Patent [19]
Collard, Jr.

[11] Patent Number: 5,662,248
[45] Date of Patent: Sep. 2, 1997

[54] SAMPLER FOR LIQUIDS

[76] Inventor: Thomas H. Collard, Jr., 1901 NW. Military Hwy., #112, San Antonio, Tex. 78213

[21] Appl. No.: 565,676

[22] Filed: Nov. 30, 1995

[51] Int. Cl.[6] ............................................. B67D 5/40
[52] U.S. Cl. ........................... 222/235; 222/380; 222/385
[58] Field of Search .................................. 222/235, 333, 222/380, 382, 385, 410, 504, 464.1; 366/190, 192, 195, 196, 264

[56] References Cited

U.S. PATENT DOCUMENTS

| 1,505,930 | 8/1924 | Schreiber | 366/196 |
|---|---|---|---|
| 3,101,161 | 8/1963 | Ivarson | 222/235 |
| 4,106,116 | 8/1978 | MacKay | 366/196 |

*Primary Examiner*—Philippe Derakshani
*Attorney, Agent, or Firm*—Gunn, Lee & Miller, P.C.

[57] ABSTRACT

An apparatus for mixing and dispensing particulate-laden liquid or immiscible liquid, samples from a container or vessel. The apparatus is attached to the top of the vessel with a mixing tube extending downwardly into the liquid sample. A valve piston disposed in the tube may be moved from a closed position to an open position while the liquid sample is continuously agitated and circulated through the mixing tube. The agitation system lifts a portion of the liquid sample through the valve piston and out a discharge port for eventual assaying.

14 Claims, 3 Drawing Sheets

SAMPLER FOR LIQUIDS

BACKGROUND OF THE INVENTION

The present invention relates to a sampling apparatus and, more particularly, to an apparatus for dispensing samples of liquids containing particulate matter or immiscible liquids.

A long standing problem with existing liquid sampling techniques is obtaining a representative sample of the original liquid when such original contains suspended solids, immiscible liquids, or other particulates. The problem results from the tendency of the particulate to settle to the bottom of or at any strata in the sampling container. When a portion of the liquid is withdrawn or poured off to assay for total solids or total specific metals or ions, the assay portion is typically not representative, and inaccurate results are obtained.

The usual method for dispensing the accumulated solids in the sampling container is to agitate the container and then pour off a small portion which, in turn, is again agitated before an aliquot is taken for analysis. The first separation step allows a disproportionate amount of solid particulate to remain in the container than in the small withdrawn portion. This is further compounded when the aliquot usually contains proportionately less particulate than is in the small sample. As more individual samples are withdrawn the particulate concentration per unit volume increases because of the inadequacies of the sampling technique.

These sampling problems are particularly acute in splitting samples of waste water and in obtaining aliquots of them. Standard samplers for waste water usually collect composite samples into ten-liter containers, or aliquots may be taken from small laboratory glassware. Currently there is no sample splitter design available which may be utilized in a broad range of sampling operations.

A further requirement for an effective sampling apparatus is simplicity of construction. A sampler must be capable of easy assembly and disassembly for cleaning purposes. Because any sampling results are adversely affected by contamination, the sampling apparatus must be thoroughly cleaned after each usage. In sampling waste water, particulate matter tends to adhere to container surfaces and lodge in complex valving. Difficulties in removing such particulate buildups on existing sampling apparatuses is well known. The present invention involves the use of an apparatus which is easily disassembled and made of polypropylene or other materials which may be coated to further reduce particulate buildup.

SUMMARY OF THE INVENTION

The present invention provides an apparatus for dispensing a particulate-laden, or immiscible liquid-laden, liquid sample from a container or vessel. The instant invention is attached to the open top of the container of liquid sample. A hollow mixing tube extends downwardly into the liquid sample and is provided with a valve piston disposed inside the upper end of the tube. An agitator drive shaft is arranged to extend downwardly through the central axis of the valve piston with propeller blades affixed near the end of the shaft. The liquid sample is continuously agitated to ensure representative distribution of the particulate or immiscible liquid within the overall liquid during the dispensing of a sample portion.

A sample portion of the particulate-containing, or immiscible liquid-laden, liquid may be dispersed by moving the valve piston within the tube from a first, closed position to a second, open position. As the valve piston is moved from the first position to the second position the outer portion of the valve piston body covers a first set of circulation ports and opens both a fluid passage and a discharge port. The agitating propellers not only continue to mix the liquid/particulate/immiscible liquid, but provide the motive force to lift a portion of the liquid sample causing it to flow from inside the mixing tube through the fluid passage and out the discharge port. The dispensed liquid sample containing the particulate or immiscible liquid is then assayed using conventional analytical techniques.

The continuous agitation during the dispensing overcomes the settling problem noted in the prior art techniques. Further, the present invention is designed to be built in various sizes in order to be received on a wide range of container sizes, thereby providing a design versatility not previously known. The construction of the present invention enables it to be quickly disassembled, cleaned, dried, and reassembled to avoid contamination.

DETAILED DESCRIPTION OF THE PREFERRED EMBODIMENT

Figure 1:
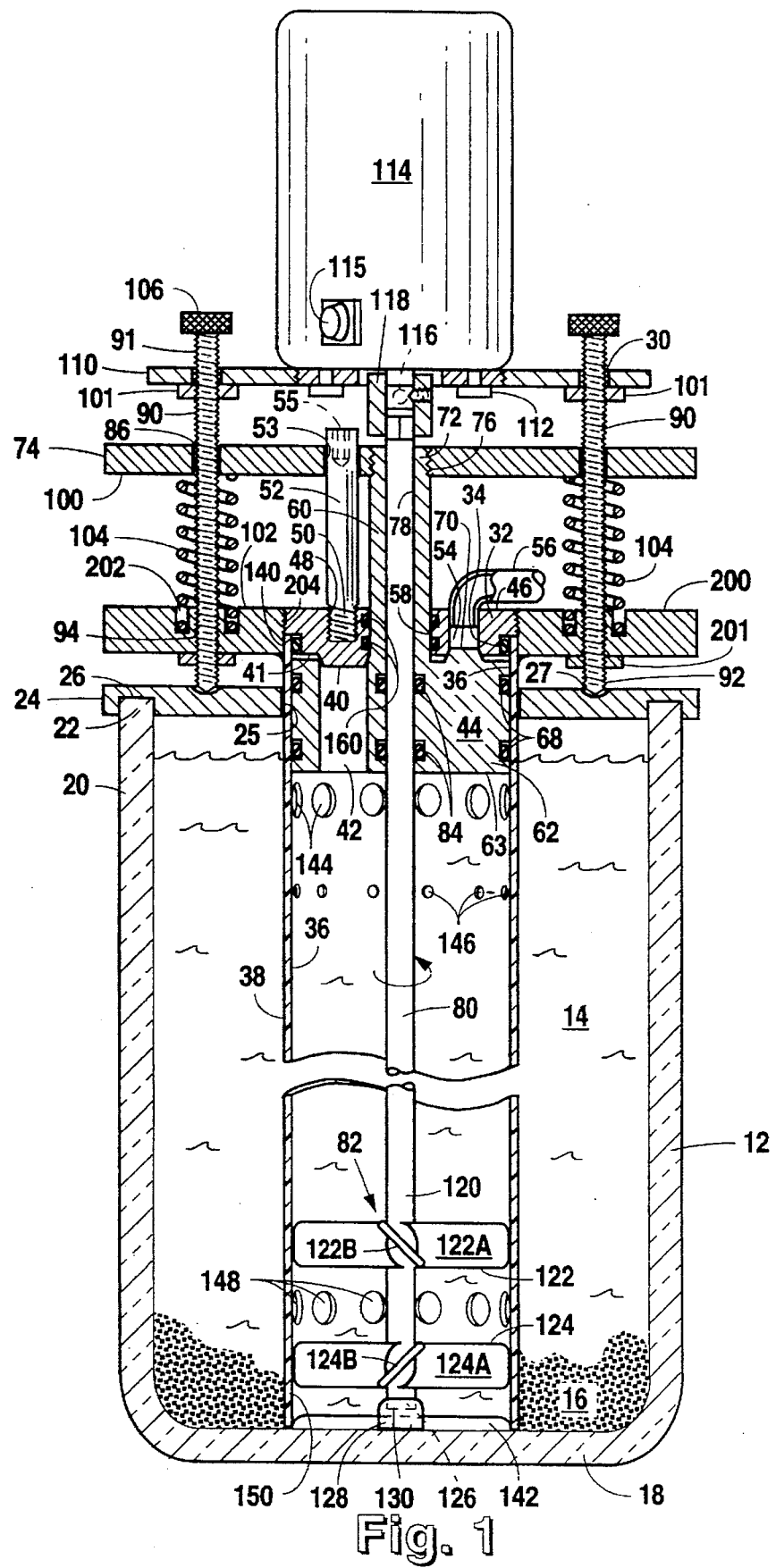
FIG. 1 illustrates a cross-sectional elevation view of the present invention with the agitator turned off.

FIG. 1 illustrates the present invention in a cross-sectional elevation view of a preferred embodiment with a ten-liter container. A container 12 is shown with a liquid sample 14 having a particulate or immiscible liquid 16 which has settled to the bottom 18 of the container after having been taken from the source, for example, a waste water source. It should be understood throughout this discussion that where the term particulate is used it includes immiscible liquid and suspended solids.

The container 12 has an open top 20 with a rim 22. The container for the liquid sample may be of any size but is typically in the range of a 10 liter jar to a 100 milliliter laboratory flask or beaker.

A cap plate 24 having a circumferential groove 26 may be positioned on the container 12 with the rim 22 fitted into the groove 26. Thus, depending on the size of the container rim opening, the diameter of the circumferential groove will vary to accept the rim. In the preferred embodiment the groove 26 is not threaded to facilitate mounting the support on the rim. However, it should be understood that in some applications groove 26 may be threaded to accept mating threads at the rim area of the container.

Cap plate 24 is a generally circular disk of polypropylene approximately 0.375" thick and having an overall diameter of approximately 5.000" for a ten-liter container. However, it should be understood that the thickness and diameter will vary appropriately according to the size of the container. The outer edge of groove 26 has inner and outer diameters to provide a groove appropriate for the container. Plate 24 further has a center bore 25 which allows the mixing tube 38 to slide through it when the present invention is assembled or the distal end of the tube 38 is adjusted.

A support plate 200 is held in a variable spaced-apart relationship from a cap plate 24 by screws 90 passing through threaded bores 94 in support plate 200 and knurled lock nuts 201. Plate 200 further has a center threaded bore 204 which retains center plug 32 in threaded engagement when the present invention is assembled.

Center plug 32 is provided with a sealing O-ring 34 for sealing engagement with the inner surface 36 of mixing tube 38. A cap valve seat 40 is formed in the underside 41 of the center plug 32 for sealing engagement with a fluid passageway 42 in the valve piston 44 when the valve piston 44 is in a first, closed position as will be further discussed below. An alternative means for forming a sealing engagement between the center plug 32 and the passageway 42 in the first, closed position is to provide an O-ring seal in an O-ring groove in the plug 32 with the diameter of the O-ring seal appropriate for sealing the passageway 42 as is well known in the art.

The top side 46 of center plug 32 is provided with a threaded hole 48 to receive and retain the threaded end 50 of a guide pin 52. Guide pin 52 is attached and removed with a hex key wrench which may be inserted in hex opening 55.

Discharge port 54 extends entirely through plug 32 and a discharge conduit 56 is received into the port 54 to transport a dispensed sample portion of the particulate-laden liquid sample to another container for final assay, as will be discussed.

Center plug 32 in the preferred embodiment is approximately 2.000" in diameter and further is provided with an approximate 0.500" central, valve piston journal bore 58 which allows the valve piston journal 60 to slidingly reciprocate within bore 58 when the valve piston 44 moves between the first, closed position and a second, open position inside of mixing tube 38. Journal 60 is sealed within center plug 32 by appropriate O-rings 160.

FIG. 1 illustrates the valve piston 44 in the first, closed position. Valve piston 44 is preferably made of polypropylene. Valve piston 44 has a cylindrical body section 62 with O-rings 68 set into ring grooves along the outer surface of the body section 62. O-rings 68 are provided to sealingly engage against the inner surface 36 of the mixing tube 38. Valve piston 44 is further provided with a discharge valve seat 70 formed in the top side of piston 44 for sealing engagement with discharge port 54 in center plug 32 of support plate 200 when the valve piston 44 is in its first, closed position. As with a cap valve seat 40, discharge valve seat 70 may be alternatively formed by providing O-ring grooves and seals in the top side of valve piston 44 with diameters appropriate for sealing the discharge port 54.

Extending upwardly from the top side of valve piston 44 is piston journal 60. Top end 72 of journal 60 is threaded to be threadingly attached centrally to valve plate 74 in opening 76 so that when valve plate 74 is moved upwardly or downwardly, journal 60 slides within bore 58 of plug 32 to move valve body 44 upwardly or downwardly while being sealed by O-ring seals 160. Journal 60 is provided with an axial bore 78 which extends through the journal 60 from the top end 72 of the journal all the way through the body 62 of piston valve 44 to the underside 63 of the valve 44. This bore 78 allows the drive shaft 80 of agitator 82 to pass through the valve piston 44. O-ring seals 84 are provided in bore 78 within the body portion 62 of valve piston 44 to sealingly engage about drive shaft 80. In the preferred embodiment bore 78 is approximately 0.250" while the diameter of journal 60 is approximately 0.500".

Figure 3:
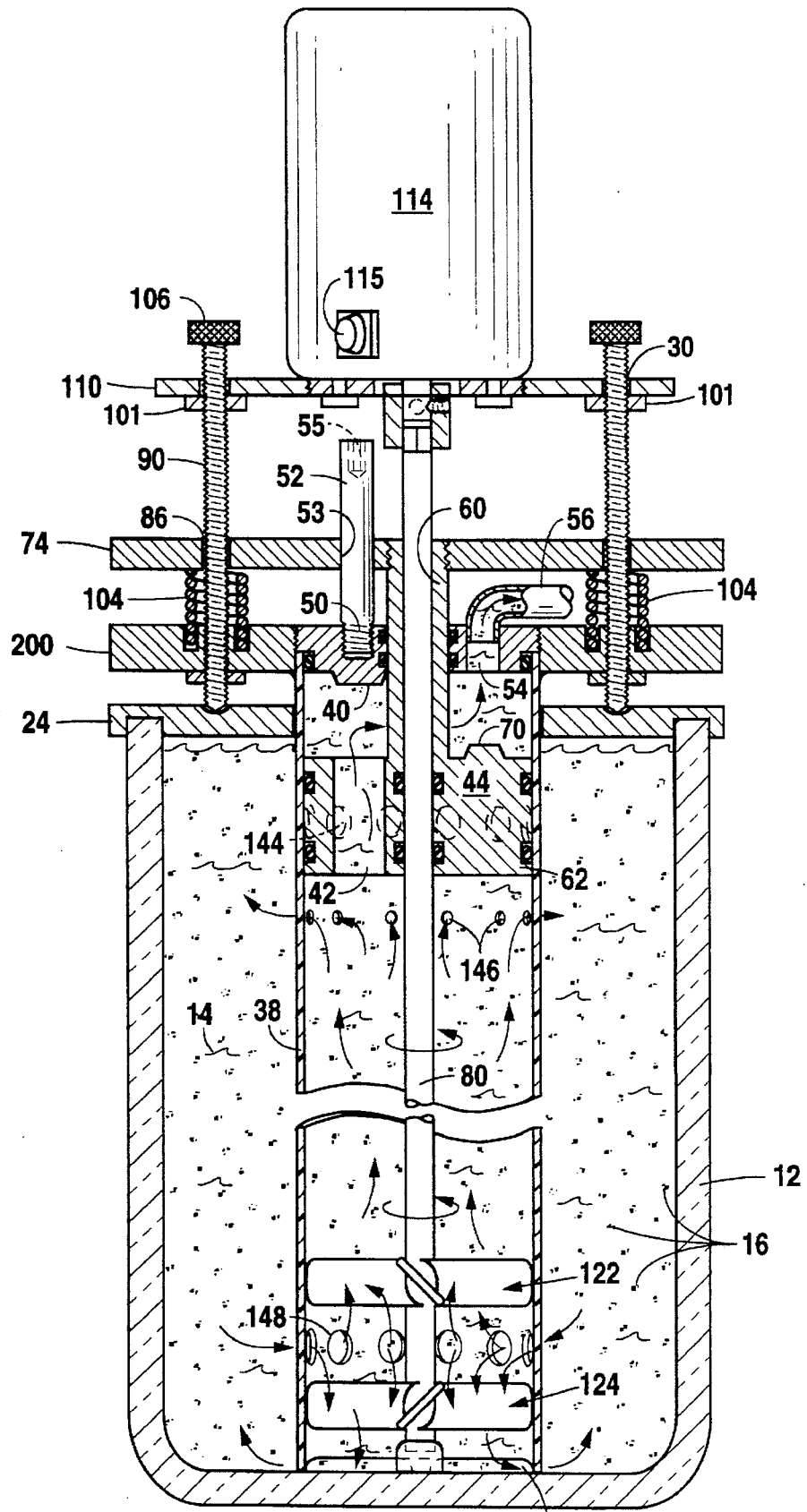
FIG. 3 illustrates a cross-sectional elevation view of the present invention with the agitator turned on and the valve piston in the second, opened position.

Valve piston 44 is provided with a fluid passageway 42 to allow a portion of the liquid sample to pass from inside the mixing tube 38 beneath the valve to above the valve and out discharge port 54 when the valve is open, as in FIG. 3. In the preferred embodiment passageway 42 is approximately 0.375" in diameter. Passageway 42 is axially aligned with cap valve seat 40 so that when the valve piston is in its first, closed position cap valve seat 40 is sealingly engaged to shut off or close passageway 42, and is kept in alignment by guide pin 52.

As previously discussed valve plate 74 is centrally attached to journal 60. Valve plate 74 is further provided with guide pin opening 53 through which extends guide pin 52. Guide pin 52 is of sufficient length to extend above valve plate 74 when the valve plate 74 and valve piston 44 are in either the first, closed position or the second, open position. In the preferred embodiment guide pin 52 is approximately 1.750" in length and has a diameter of approximately 0.250". Guide pin opening 53 is approximately 0.254" in diameter.

Three knurled head screw openings 86 are provided through valve plate 74 about 120° apart on an arc having a radius of approximately 1.625" from the center of plate 74 in the preferred embodiment. (The figures show only two of these screw openings.) The upper ends of screws 90 are able to pass through openings 30 in motor support plate 110 and openings 86 in valve plate 74. The lower ends of screws 90 threadingly pass through threaded bore 94 in support plate 200 and the distal end 92 Of screws 90 are in rotatable contact with dimples 27 formed in cap plate 24. Disposed beneath the underside 100 of valve plate 74 and between the upper side 102 of support plate 200 are helical compression springs 104. Screws 90 pass through the central axis of the helical springs 104 and hold the springs in place. The springs 104 press or urge against the underside 100 of the valve plate 74 and the upper side 102 of support plate 200 in spring retaining grooves 202 to hold valve piston 44 in the normally closed position.

At the top end 91 of screws 90 are knurled heads 10. Screws 90 cooperate with support nuts 101 to hold motor support plate 110 in a spaced relationship above cap plate 24 and allow for adjustment of the distal end 150 of the mixing tube 38, as will be discussed below. Suitable motor mount screws 112 retain an agitator motor 114, on motor mount plate 110, with the motor shaft 116, in axial alignment with drive shaft 80. Coupling 118 couples the motor shaft to the propeller drive shaft 80 to translate rotary power from the motor to the propellers 122 and 124, as is well known in the art. In the preferred embodiment the motor is a 12 v. D.C. motor; however, any motor capable of driving the propellers 122 and 124 may be utilized, including a battery driven electric motor or even an air motor controlled by a push-to-open air valve.

Motor 114 is provided with a push button normally open activation switch 115. This safety feature insures that the motor is off if the operator's finger slips off the switch 115.

Support plate 200 may be raised or lowered by adjustment of screws 90 and knurled lock nuts 201. Movement of support plate 200 in turn raises or lowers the distal end 150 of the mixing tube 38.

The lower end 120 of drive shaft 80 is provided with an impeller including propellers 122 and 124. Upper propeller 122 has blade sets 122A and 122B having pitch angles of approximately 45° and a blade face width of 0.500". It should be understood that various pitch angles and face widths may be used to increase or decrease the agitation turbulence when the impellers are operating. Lower blade sets 124A and 124B are spaced below upper sets 122A and 22B by approximately 0.675" and are pitched opposite the pitch of the upper blades to provide two-direction flow or circulation. This arrangement allows a portion of the sample liquid to be pushed downwardly by the lower blades and upwardly by the upper blades. Such an arrangement improves the circulation of particulate-laden liquid within the container 12 and mixing tube 38, as will be discussed below.

The distal end 126 of shaft 80 is inserted into a shaft support 128 fitted and attached into the end of mixing tube 38 to provide a bearing support surface 130 for maintaining axial alignment of distal end 126 within the tube 38.

Mixing tube 38 is a generally hollow tube which is disposed within the container 12 by fusion at its top end 140 to support plate 200 near O-ring seal 34. The tube 38 extends downwardly and rests on the bottom 18 of the container 12 with a gap opening 142 formed between the bottom 18 of the container 12 and the tube 38. Valve piston 44 slides inside of mixing tube 38, as has been discussed.

A first upper set of circulation ports 144 is formed in the walls of the tube 38 near the top end 140 of the tube. In the preferred embodiment the tube 38 is approximately 12.000" long and has an inside diameter of approximately 1.875" and an outside diameter of approximately 2.000". The tube is made of polypropylene.

There are approximately twelve 0.250" diameter circulation ports 144 formed in the upper wall section of tube 38 at 30° apart. Approximately 0.750" below the first set of circulation ports is a set of intermediary, smaller, circulation ports 146. Intermediary ports 146 in the preferred embodiment are approximately 0.060" in diameter set at 30° apart. These twelve intermediary ports provide for reduced, but continued circulation of particulate-laden liquid within the tube 38 and container 12 when valve piston 44 is in its second, open position.

A second, lower set of circulation ports 148 is formed in the lower wall of the tube 38 near the distal end 150 of the tube. In the preferred embodiment the lower circulation ports 148 are spaced approximately 1.000" above the bottom end of the tube and approximately 9.000" below the intermediary circulation ports. There are twelve 0.250" diameter lower circulation ports 148 formed in the lower wall of tube 38 at 30° apart at the distal end 150 of the tube 38. Thus, as may be seen in FIGS. 1–3, the second set of ports 148 is located between the first and second set of propellers 122 and 124.

Figure 2:
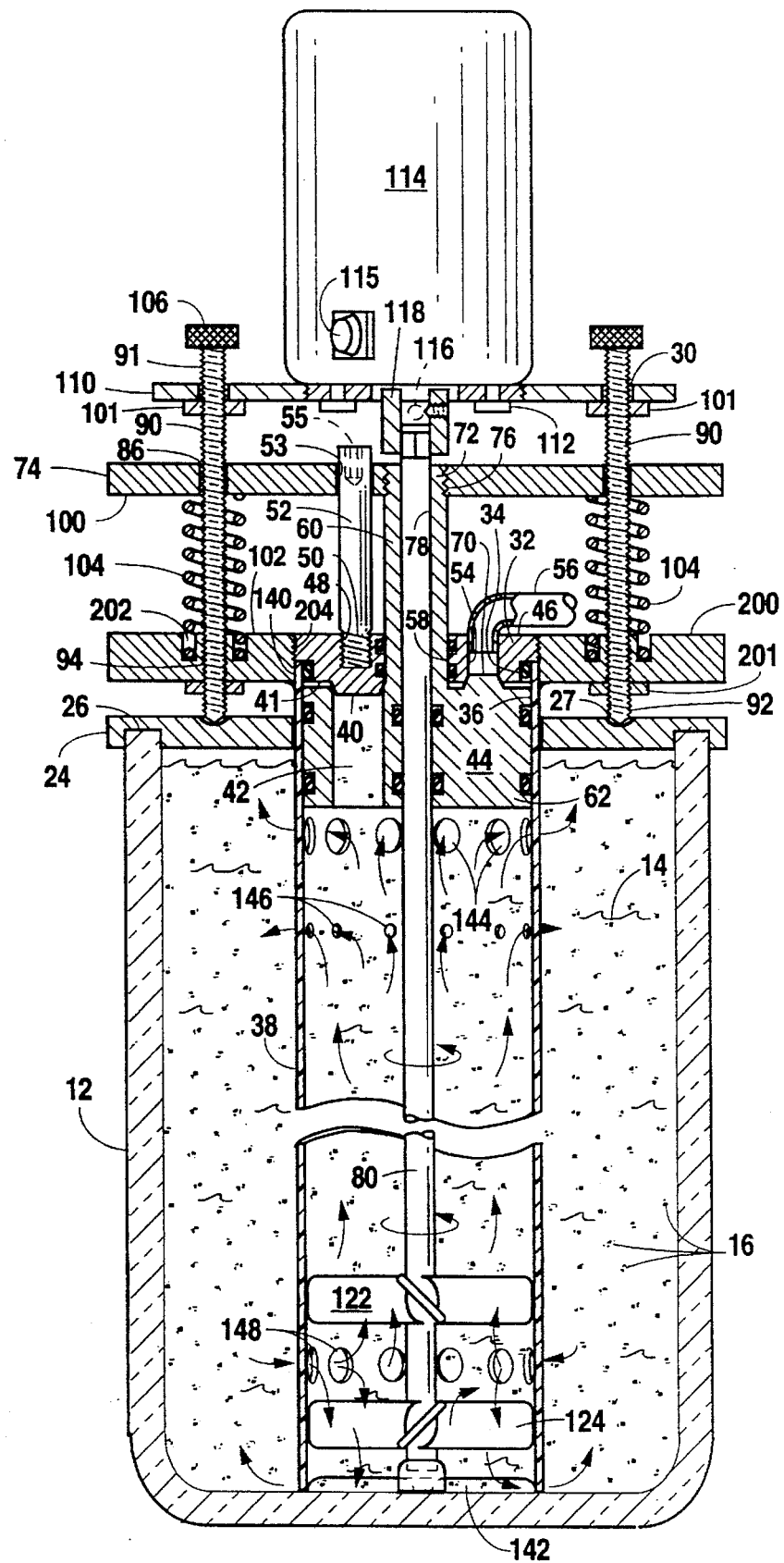
FIG. 2 illustrates a cross-sectional elevation view of the present invention with the agitator turned on and the valve piston in the first, closed position.

Turning to FIG. 2, it may be seen that the agitator motor 114 has been activated by pressing push-button switch 115 and the drive shaft 80 is rotating in a counterclockwise direction as viewed from above. (Upon release of switch 115, the motor 114 is deactivated.) The particulate or immiscible liquid 16 has been evenly distributed throughout the sample liquid 14 in the container 12 and mixing tube 38. The lower propeller blades 124 are shown forcing the particulate-laden liquid to be circulated in through the second, lower set of circulation ports 148 and out the gap 142 at the bottom of the tube 38.

The particulate-laden liquid is also drawn into lower ports 148 and forced upwardly in mixing tube 38 by the upper set of propeller blades 122. The liquid with particulate is circulated through the intermediary ports 146 into the container 12 and through the first, upper set of circulation ports 144. The swirling action normally associated with existing agitators is essentially eliminated by the arrangement of the ports 148, 146, and 144 and the propellers 122 and 124, thereby providing proper and even distribution of the particulate or immiscible liquid within the liquid sample.

In FIG. 2 valve piston 44 is shown in the first, closed position with the passageway 42 sealed by cap valve seat 40, and discharge port 54 sealed by discharge valve seat 70. Springs 104 are urging the valve plate 74 upwardly. Valve seats 40 and 70 are maintained in axial alignment by guide pin 52 extending through guide opening 53.

In FIG. 3, valve plate 74 is shown moved to its second, open position. Plate 74 has been manually pushed downwardly toward cap plate 24. Springs 104 have been compressed, and guide pin 52 has been extended further through guide pin opening As a result of urging plate 74 downwardly, journal 60 and valve piston 44 have also moved downwardly. The body 62 of valve 44 has moved to cover the upper circulation ports 144. However, the smaller, intermediary ports 146 remain uncovered, and the particulate-laden liquid 14 continues to circulate through the container 12 and mixing tube 38 as a result of the continued agitation of the liquid by the agitation system.

The movement of valve piston 44 to this second, open position shown in FIG. 3, unseats cap valve seat 40 from passageway 42, allowing evenly distributed, particulate-laden liquid to flow through the passageway 42 to a region above the valve piston 44. Discharge port valve seat 70 is simultaneously unseated from discharge port 54, opening the port 54 to allow a portion of the particulate-laden liquid sample to pass through discharge conduit 56 while the agitation process is continued. Mixed sample liquid will continue to flow out discharge port 54 so long as the valve piston 44 is maintained in the second position because the propellers 122 continue to lift and agitate the liquid sample.

Upon release of the downward force on valve plate 74, springs 104 immediately urge the valve piston 44 to its first, closed position, sealing the passageway 42 and discharge port 54, and terminating the dispensing of the liquid sample. Upper ports 144 are uncovered and circulation of the particulate-laden liquid continues so long as the push-button switch 115 is closed.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

I claim:

1. An apparatus for dispensing a portion of a liquid sample from a container comprising:

a generally hollow tube disposed within said container, said tube having a first end and a second end, said first end attached to a cap plate releasably attachable to an open top of said container, said cap plate having a discharge port and a cap valve seat, said tube having a first set of ports disposed near said first end of said tube, a second set of ports disposed near said second end of said tube, and a set of intermediary ports disposed between said first and said second set of ports;

a valve piston disposed within said tube movable from a first position to a second position, said valve piston having a passage for fluid communication from a bottom side of said valve to a top side of said valve piston, said passage axially aligned with said cap valve seat, and said valve piston having a discharge port seat, said seat axially aligned with said discharge port in said cap;

a means for continuously agitating remaining liquid sample in said container during dispensing of said portion of said sample liquid; and a means for moving said valve piston from said first position to said second position wherein when said valve piston is in said first position said first set of ports are uncovered to allow continuous circulation of said liquid sample through tube and said container with discharge port seat seated in said discharge port and said cap valve seat seated in said passage and said liquid sample may not be dispensed from said container, and when said valve piston is in said second position said first set of ports are covered, said discharge port seat is unseated, said cap valve seat is unseated, thereby allowing said portion of liquid sample to be dispensed from said container while a remaining portion of liquid sample circulates through said second set of ports and said intermediary ports in said tube.

2. The apparatus of claim 1 wherein said means for moving said valve piston from said first position to said second position further comprises:

a valve plate;

a central journal extending upwardly from a top side of said valve piston and attached along an underside of said valve plate, said journal slidable within an axial bore in said cap plate to move said valve piston from said first position to said second position;

a spring member urging against a top side of said cap plate and along said underside of said valve plate to urge said valve piston in said first position.

3. The apparatus of claim 1 further comprising a means for maintaining alignment of said passage in said valve piston with said cap valve seat and said discharge port seat with said discharge port in said cap plate.

4. The apparatus of claim 2 wherein said alignment means further comprises a guide pin attached to said top side of said cap plate and slidably passing through a guide opening in said valve plate.

5. The apparatus of claim 1 wherein said agitating means further comprises:

a motor;

a drive shaft coupled at a first end to said motor;

an impeller attached near a second end of said shaft, said drive shaft passing through an axial bore in said journal and said valve piston so as to dispose said impeller centrally within said tube near said second set of ports; and means for activating said motor to rotate said shaft and impeller.

6. The apparatus of claim 5 further comprising:

a drive shaft support member attached to said second end of said tube, said support member having a bearing support surface for maintaining the distal end of said drive shaft in axial alignment within said tube.

7. The apparatus of claim 5 wherein said impeller comprises:

a first set of propeller blades disposed around said drive shaft at a first angle of inclination, and a second set of propeller blades disposed around said drive shaft below said first set of propeller blades at an inclination angle different than said first angle of inclination.

8. The apparatus of claim 7 wherein said angle of inclination of said second set of propeller blades is generally opposite said first set of propeller blades to provide two-direction circulation.

9. The apparatus of claim 5 further comprising:

a motor mounting plate spaced above said cap plate and said valve plate for supporting said motor;

a plurality of wing screws and wing nuts for supporting said mounting plate in said spaced relationship, said screws connected to one end to said top side of said cap plate, said spring member comprising a plurality of helixially wound compression springs, said screws passing through the central axis of said compression springs.

10. The apparatus of claim 1 wherein said cap valve seat and said discharge port seat are O-ring seals.

11. The apparatus of claim 1 wherein said intermediary ports are smaller in diameter than said first set and said second set of ports.

12. The apparatus of claim 1 wherein said liquid sample contains particulates or immiscible liquids.

13. The apparatus of claim 5 wherein said activating means is activated by engaging a push button and deactivated upon release of said push button.

14. The apparatus of claim 1 further comprising a means for vertical adjustment of said tube to meet the requirements of a multiplicity of containers.

* * * * *